United States Patent
Christensen et al.

(10) Patent No.: US 6,482,184 B1
(45) Date of Patent: Nov. 19, 2002

(54) ATTACHABLE CATHETER

(75) Inventors: James Christensen, Glendora, CA (US); H. William Reese, Tempe, AZ (US)

(73) Assignee: Advanced Infusion, Inc., Tempe, AZ (US)

( * ) Notice: Subject to any disclaimer, the term of this patent is extended or adjusted under 35 U.S.C. 154(b) by 102 days.

(21) Appl. No.: 09/675,758

(22) Filed: Sep. 29, 2000

(51) Int. Cl.$^7$ ............................................... A61M 5/32
(52) U.S. Cl. ........................................ 604/174; 604/131
(58) Field of Search ........................... 604/174, 176, 604/179, 131

(56) References Cited

U.S. PATENT DOCUMENTS

| | | | | | |
|---|---|---|---|---|---|
| 4,311,148 A | * | 1/1982 | Courtney et al. | ........... | 128/348 |
| 5,527,293 A | * | 6/1996 | Zamierowski | ............... | 604/176 |
| 5,782,747 A | * | 7/1998 | Zimmon | ........................ | 600/104 |
| 5,954,694 A | * | 9/1999 | Sunseri | ......................... | 604/96 |
| 6,042,577 A | * | 3/2000 | Chu et al. | ..................... | 604/523 |
| 6,258,061 B1 | * | 7/2001 | Drasler et al. | ............... | 604/131 |
| 6,302,875 B1 | * | 10/2001 | Makower et al. | ........... | 604/528 |
| 6,315,789 B1 | * | 11/2001 | Cragg | ........................ | 606/232 |
| 2002/0007130 A1 | * | 1/2002 | Burbank et al. | ............. | 600/564 |

* cited by examiner

Primary Examiner—Denise L. Esquivel
Assistant Examiner—Marc Norman
(74) Attorney, Agent, or Firm—Koppel, Jacobs, Patrick & Heybl; Michael J. Ram

(57) ABSTRACT

A new and improved tube or catheter for administrating or withdrawing a substance from the human body which can be temporarily attached to the tissue site. The catheter consists of a dual lumen, side-by-side, tube. One lumen is used to administer or withdraw a substance. The second lumen contains an attachment means consisting of a loop of filament extending beyond the both ends of the lumen in the second tube. During use the surgeon fixes a suture at the tissue site and ties the suture around the filament loop extending from the distal end of the second tube. The surgeon then grasps the proximal end of the filament and slides the catheter over the filament and the suture until it rests against the tissue attachment site. The filament or suture is then tied around the proximal end of the tube to hold the catheter in place. To remove the catheter, the surgeon cuts the suture where tied to the proximal end of the tube, pulls off the catheter, and slides the suture out of the tissue.

9 Claims, 7 Drawing Sheets

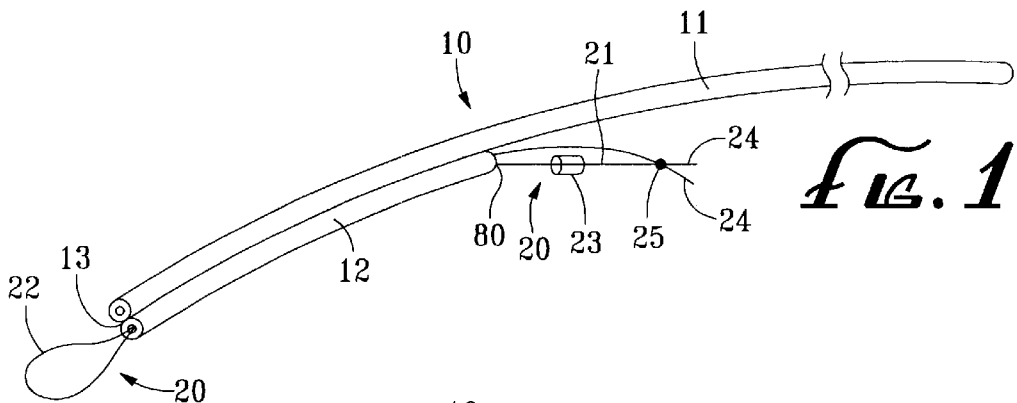
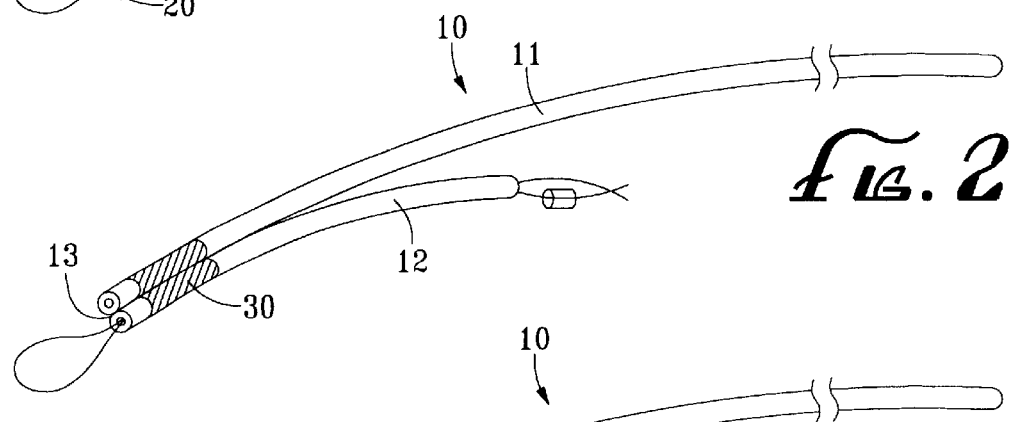
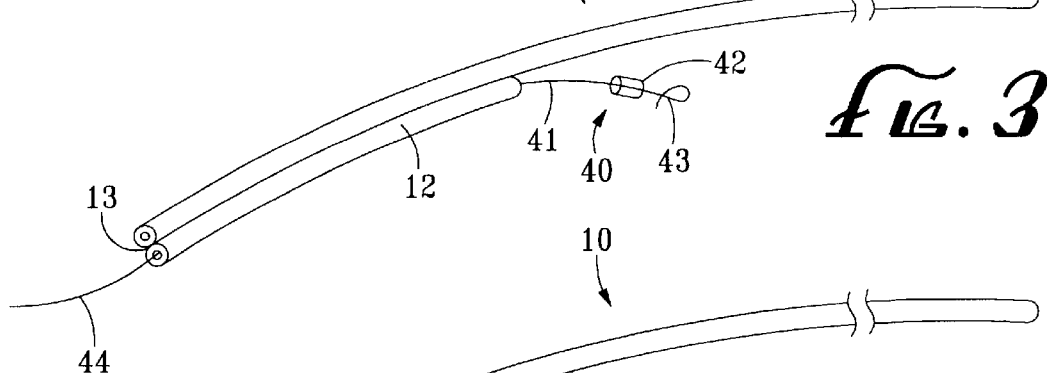
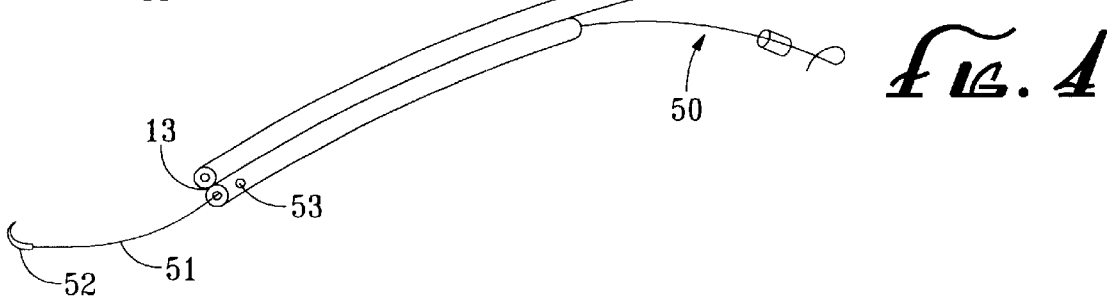

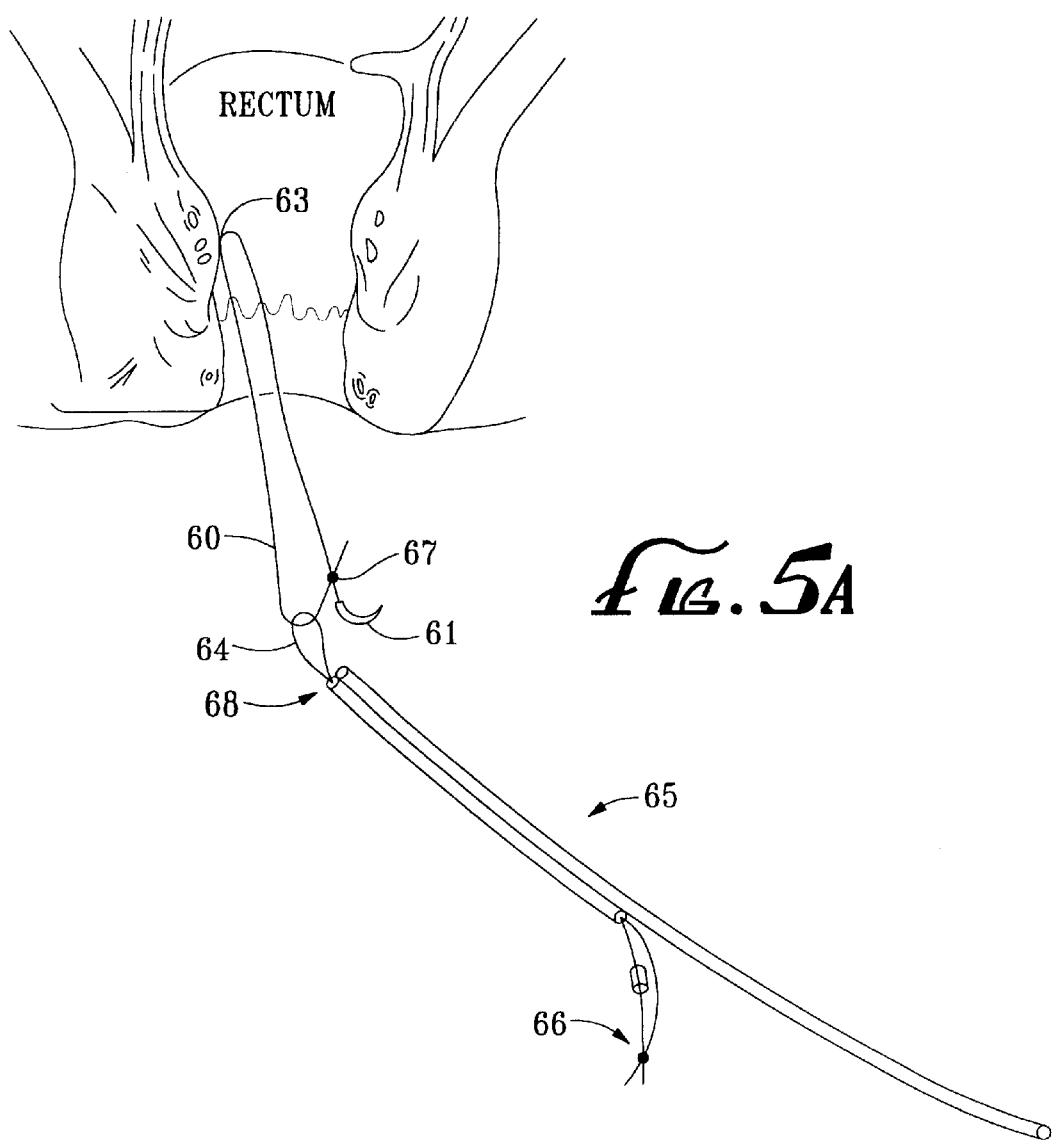

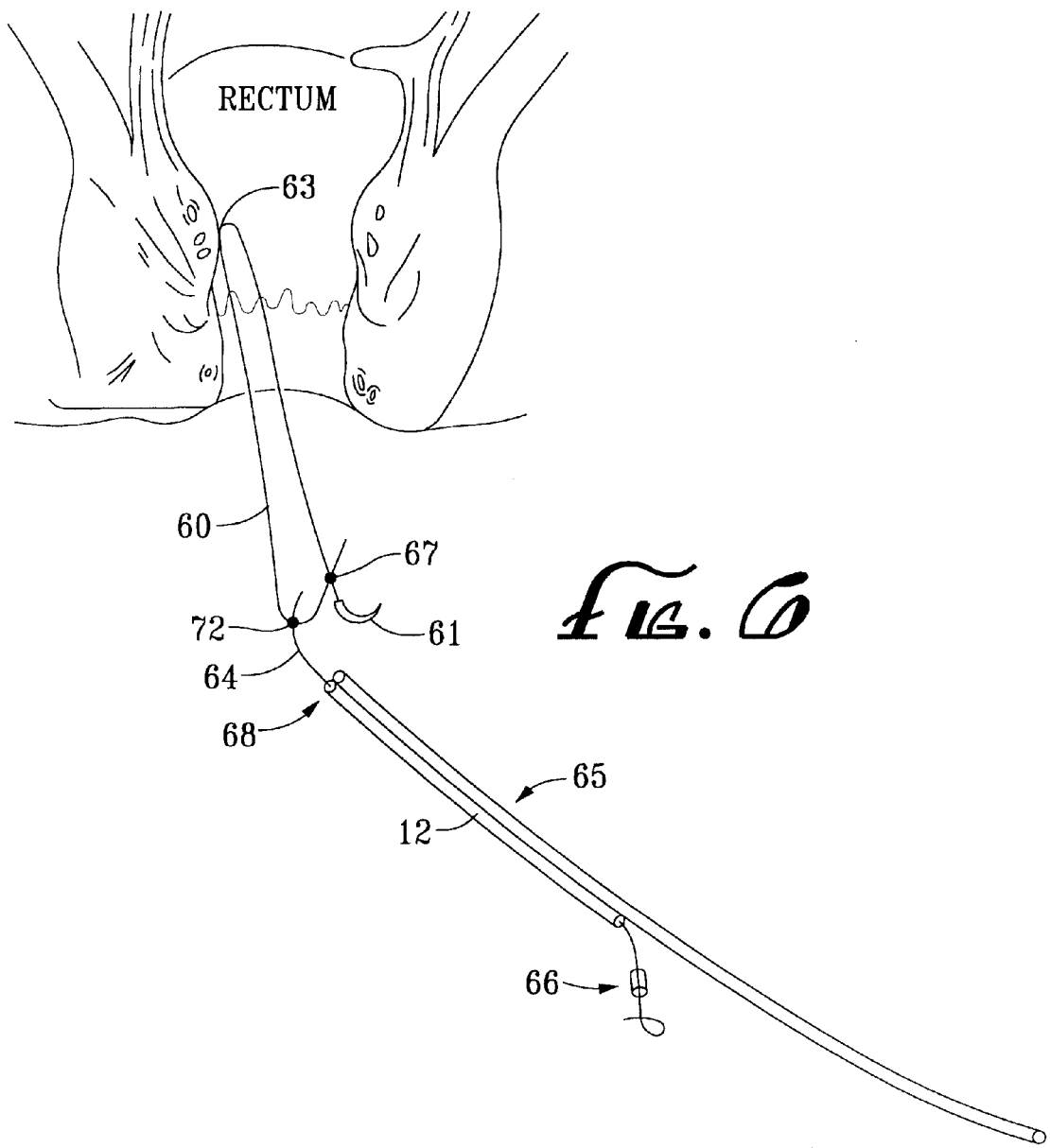

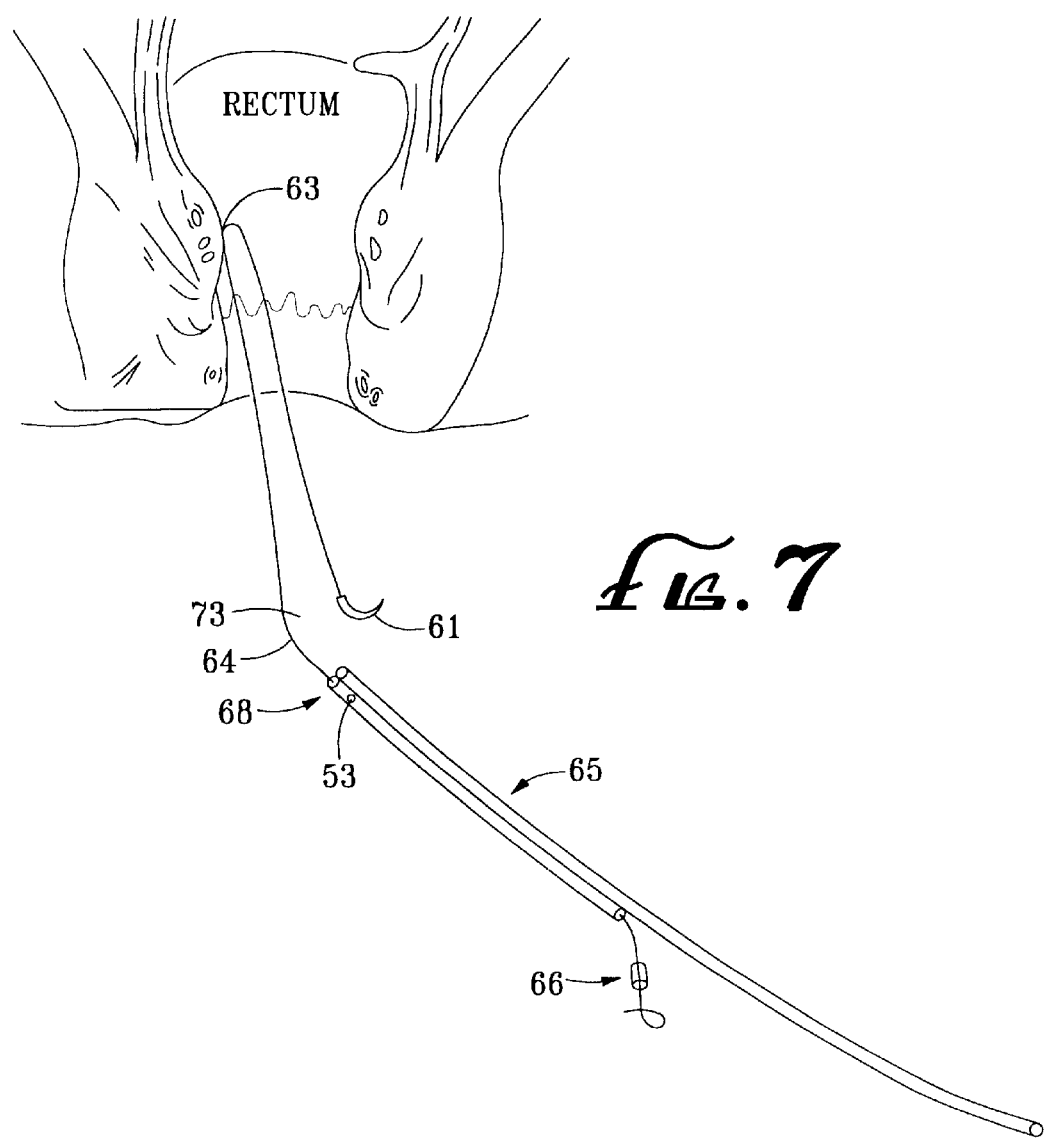

ATTACHABLE CATHETER

BACKGROUND OF THE INVENTION

1. Field of the Invention

The present invention relates to a tube or catheter, and more particularly to a tube or catheter, which can be temporarily attached to a tissue site within the human body for infusion or withdrawal of a substance from the body.

2. Description of the Prior Art

Known methods of attaching a tube or catheter into the body involve suturing the catheter into place at the attachment site. However, since sutures can not be placed through the catheter, sutures are tied or otherwise secured around the outside of the catheter to hold it in place. Slippage of the catheter and collapsing of the tube are potential problems. To remove the catheter either surgical intervention is required or, if the catheter is pulled out, the sutures used to hold the catheter in place are left in-situ.

The patent literature describes several styles of catheters which can be fixated in the body while they are used to administer or withdraw a substance from the body. Balloon catheters, as described in U.S. Pat. No. 5,954,694 to Sunseri, and other similar patents, can be fixated in a vessel or body space (i.e. abdomen) by inflating a balloon at or near the distal end of the catheter. Additional lumens in the catheter can then be used to perform a variety of functions such as infusing and/or removing substances from the body or conducting a surgical procedure. However, when placed in vessels, these catheters function by occluding the vessel they are fixated in and therefore do not allow the normal functioning of the vessel to proceed. For instance they block the flow of blood in a blood vessel, or restrict the flow of urine from the bladder, and so forth.

Percutaneous style catheters as described in U.S. Pat. No. 4,311,148 to Courtney, and other similar patents, are fixated at the site they enter the body by an ingrowth means usually consisting of a fabric patch. In use body tissue will grow into the fabric patch and secure the catheter in place. In order to remove the catheter the ingrown area must be excised away. This style of catheter is not suitable for short duration use.

U.S. Pat. No. 6,042,577 to Chu et. al., and other similar patents, discloses a catheter with a suture running internally from the proximal to the distal end. However, this suture is not used to attach the catheter to tissue. Instead, it is used to open an anchoring device, such as bendable arms, which are part of the catheter distal end.

SUMMARY OF THE INVENTION

Accordingly, it is an object of the present invention to provide a tube or catheter which can be easily and reliably attached to a tissue site for a short, temporary no duration of time for the administration and/or withdrawal of a substance in the body.

It is a further object of the present invention to provide a tube or catheter attachable to a tissue site in a hollow body organ, such that the attachment means will not block the normal functioning of that body organ during use of the catheter.

Still another object of the present invention is to provide a tube or catheter which can be easily removed from the attachment site without surgical intervention and without leaving remnants of the attachment means at the attachment site.

BRIEF DESCRIPTION OF THE DRAWINGS

The above and other objects and advantages of the present invention will become apparent from the following description when read in conjunction with the accompanying drawings wherein:

FIG. 1 is a schematic representation of a preferred embodiment of the invention, FIG. 2 is a schematic representation of a second embodiment of the invention;

FIG. 3 is a schematic representation of a third embodiment of the invention;

FIG. 4 is a schematic representation of a fourth embodiment of the invention;

FIGS. 5a–5d are schematic representations showing the insertion into and removal of the first embodiment of the invention from a hollow body organ;

FIG. 6 is a schematic representations showing insertion of the second embodiment of the invention in a hollow body organ;

FIG. 7 is a schematic representations showing insertion of a further embodiment of the invention in a hollow body organ.

DESCRIPTION OF THE INVENTION

Figure 5B:
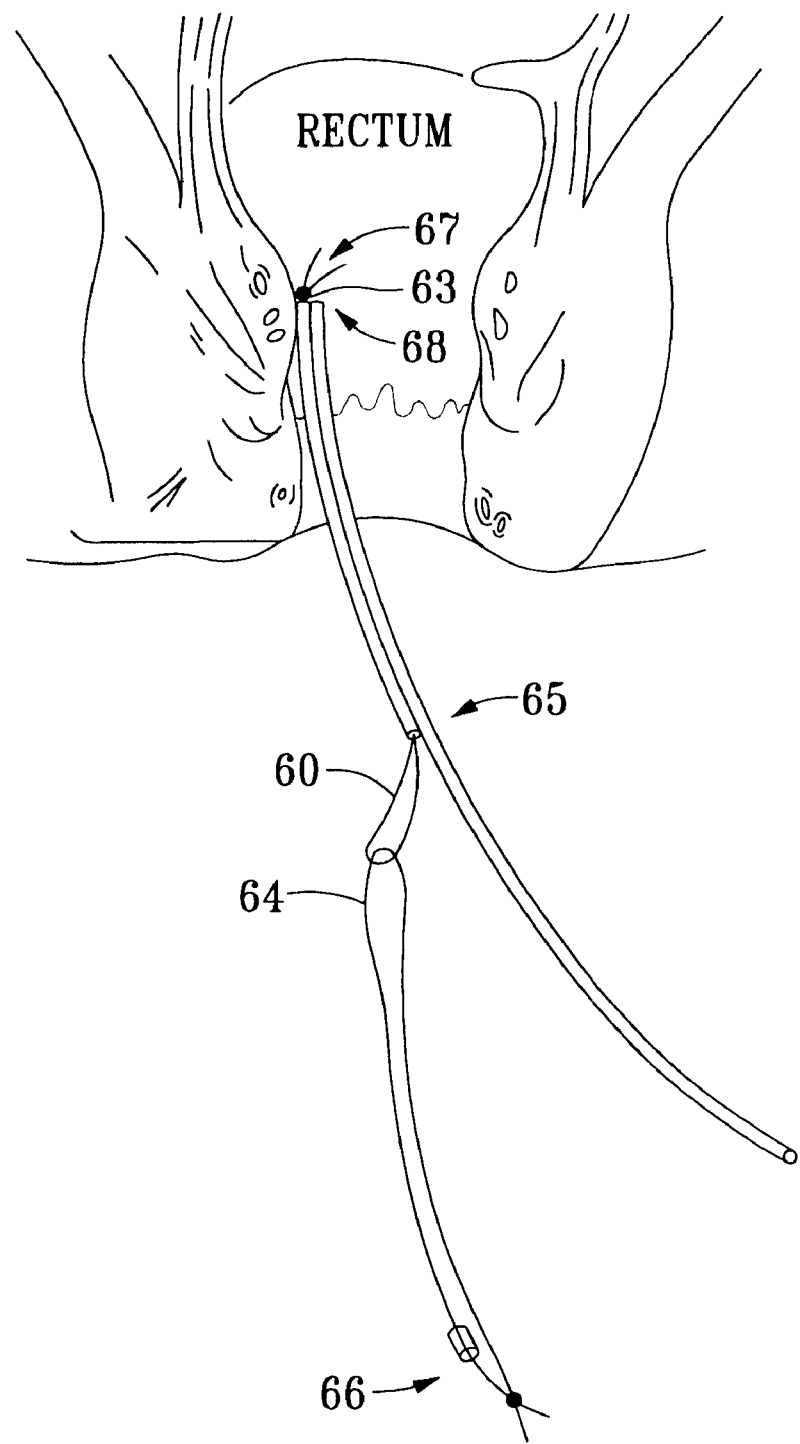

FIG. 1 shows a first embodiment of an attachable catheter 10 for administering or withdrawing a substance from the human body. The attachable catheter 10 is comprised of at least two tubes. In a preferred embodiment, a first tube is a long tube 11 and a second tube is a shorter tube 12, the tubes being mounted side by side. The distal ends 13 of both tubes are joined along a portion of their length. The long tube 11 is used to administer or withdraw a substance from the body. The shorter tube 12 is used for placement of an attachment means 20 which secures the distal end 13 of the catheter 10 in place in the body for the duration of its use.

The attachment means 20 passes through the lumen of the shorter tube 12 and extends out of both ends of that tube. In the embodiment shown, attachment means 20 consists of a length of filament 21 which is folded over and inserted through the lumen of the shorter tube 12 such that an attachment loop 22 is formed at the distal end 13 of the catheter. A retaining means such as a button 23 is placed over the end of the filament 21 exiting the proximal end 80 of the shorter tube 12 to prevent the attachment means 20 from pulling back into the short tube 12. The ends of the filament 24 extending out the proximal end may also be tied together in a knot 25 or otherwise joined beyond the proximal end 80.

The tubing forming the various embodiments of this invention can be formed from a variety of materials suitable for medical application, for example, polyurethane, silicone elastomer, Teflon, Nylon, Pebax, etc. The long tube 11 and the shorter tube 12 can be made of the same or different materials. Both the long tube 11 and the shorter tube 12 are attached along at least a portion of their length. This attachment can be accomplished by several methods. Preferably the tubes 11, 12 are extruded together as a side-by-side tube. Alternatively, the tubes can be attached after extrusion by heat, solvent, or adhesive. Still further, a single tube with two lumens may be utilized. If the tubes are extruded side by side or heat bonded together, the tube containing the filament 21 can be cut to length and the unwanted section of tubing peeled away from the long tube 11 leaving behind the shorter tube 12. While only two tubes are shown additional tubes or lumens can be provided. For example, one tube can be provided for delivery of fluid, such as an irrigation or an anesthetic fluid while a further tube can be provided to simultaneously provide drainage of fluids.

The filament forming the attachment means 20 must be of diameter suitable to fit through the lumen of the shorter tube 12 and be readily withdrawn from the tube. Materials having some stiffness are preferable for assembly of the catheter. For example, a polyester monofilament has been found most suitable for the preferred embodiment of this invention. However, more flexible filaments such as suture are also suitable alternatives. The retaining means or button 23 can be formed from any material, which will prevent the end of the attachment means from being pulled back up through the shorter tube 12. Typically, this button would be plastic or a small section of tubing. However, a knot larger than the diameter of the tube lumen would also be adequate.

FIG. 2 shows an alternative embodiment of the invention. Instead of attaching the tubes along their length, the long tube 11 and the shorter tube 12 are separately formed and attached only near their distal end 13. This attachment can be accomplished by several methods. As shown, long tube 11 and the shorter tube 12 are separately formed and attached by a band 30 of material securing the two tubes together. This band 30 can be a heat shrink plastic band or other suitable material that firmly grips and holds the tubes together. The tubes may also be bonded or glued together at the distal end 13 in place of the band.

It is not necessary that the attachment means be a looped filament. FIG. 3 shows an alternative attachment means 40 consisting of a single filament 41 passing through the lumen of the shorter tube 12. Instead of the attachment loop 22 formed in FIG. 1, the end of the filament 44 is left extending from the distal end 13 of the catheter. On the other end of the shorter tube 12, a retaining button 42 is placed over the end of filament 41 exiting the proximal end of the tube. The proximal end of filament 41 is tied in a knot 43 to prevent the attachment means 20 from pulling out of the short tube 12.

FIG. 4 shows another alternative attachment means 50. This attachment means is similar in construction to attachment means 40 shown in FIG. 3 except that the distal end 13 includes a needle 52 attached to the end of filament 51. An optional hole 53 is also provided at the distal end 13 of the catheter as an alternative means to secure the attachment means 50 as described below.

Referring to FIGS. 5a–5d, a method of attaching and removing an attachable catheter incorporating features of the invention at a site within the body is illustrated. For illustration purposes the catheter 10 is attached within the rectum and may be used to deliver an anesthetic and/or antibiotic following hemorrhoid surgery. In FIG. 5a a length of suture 60 containing a needle 61 is placed through tissue at a desired attachment site 63 inside the rectum. Both ends of the suture 60 are brought outside the anal opening, looped through the distal loop of attachment means 64, and tied together with a knot 67.

After both ends of the suture 60 are tied. The needle 61 is cut off the end of the suture and the knot 67 is pulled up into the rectum so that it is at the attachment site 63 as shown in FIG. 5b. After the knot is in place, the proximal end 66 of the attachment means is held and the catheter 65 is slid over the attachment means 64 and the suture 60 until the distal end 68 of the catheter is at the attachment site 63.

Figure 5C:
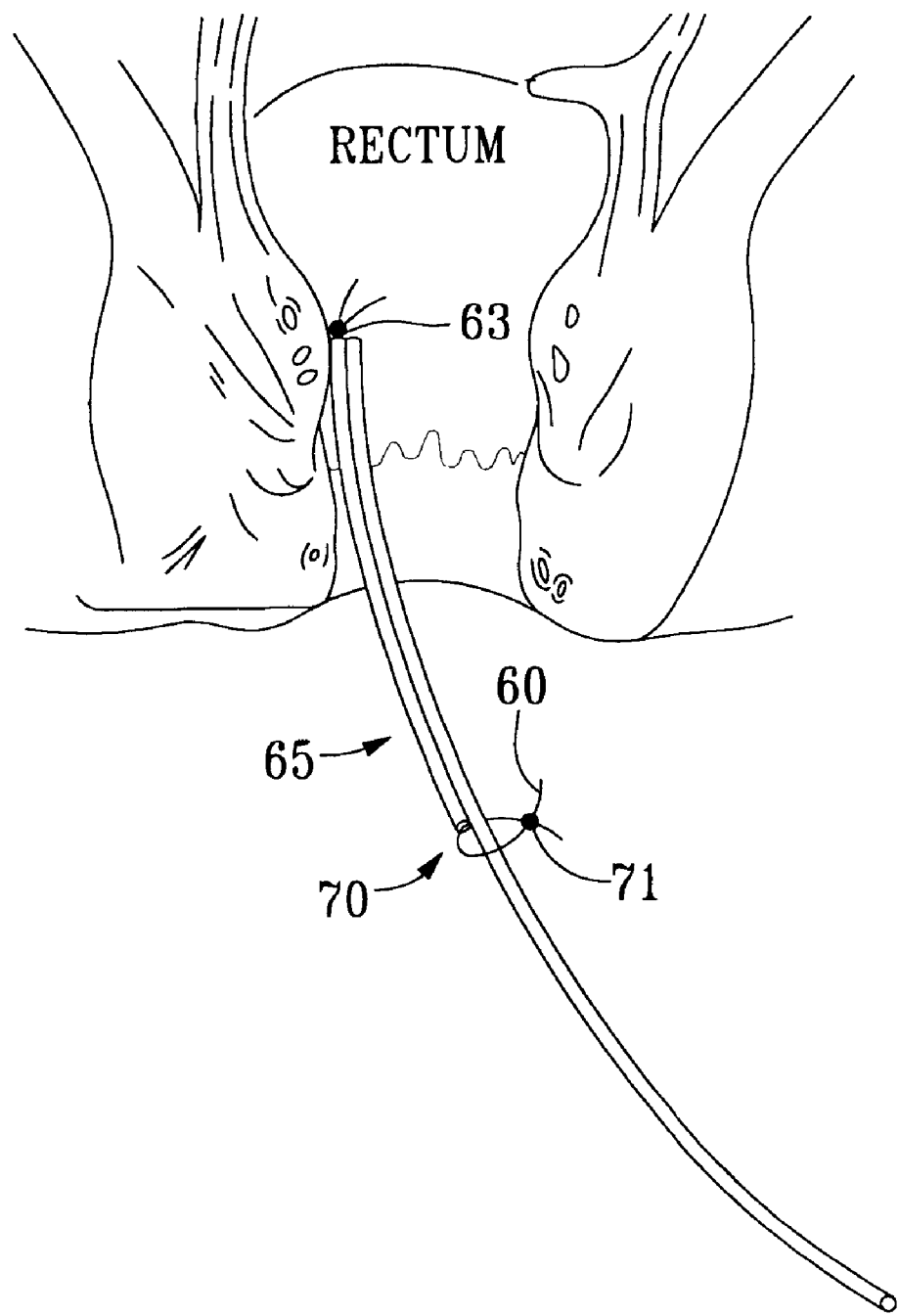

Referring to FIG. 5c, the loop of suture 60 extending beyond the proximal end 70 of the catheter is cut and the attachment means 64 is discarded. The cut ends of the suture 60 are tied together around the catheter 65 forming knot 71. This holds the catheter 65 in place at the attachment site 63. It can be seen that the catheter is held securely in place and does not block the normal functioning of the rectum since the catheter is much smaller. One skilled in the art will recognize that other means can be used to secure the proximal ends of the suture such as a clip or button.

Figure 5D:
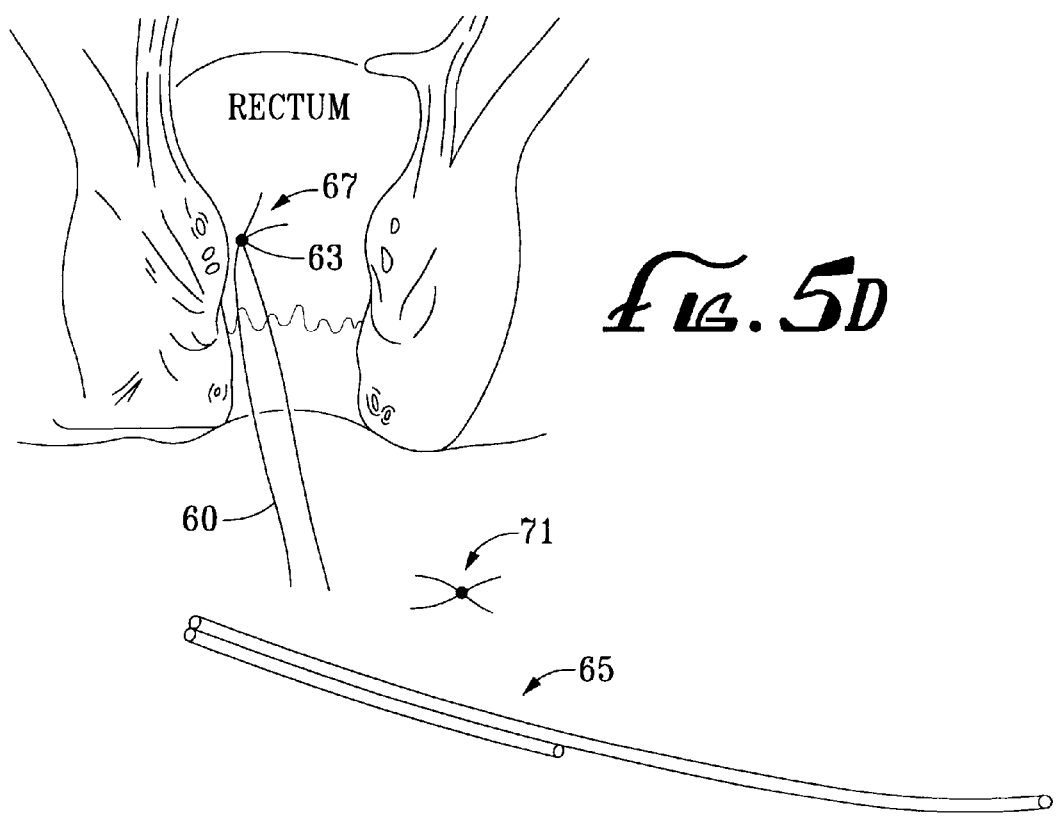

As shown in FIG. 5d, to remove the catheter 65, the knot 71 holding the proximal ends of suture 60 is completely cut off. This frees the catheter which can now be pulled out of the rectum. By grasping the end of suture 60 which contains the knot 67 at the attachment site 63 inside the rectum, the suture 60 can also be pulled from the rectum. It can be seen that all components of the catheter, its attachment means, and the attachment suture are removed from the body.

In the alternative embodiment of the attachable catheter 10 as shown in FIG. 3, the distal end of the attachment means 64 is tied to the loop of suture 60 by knot 72 as shown in FIG. 6. The needle 61 is cut from the suture and discarded. The proximal end of the attachment means 66 is held and the catheter 65 is slid over the attachment means 64 and the suture 60 until the distal end 68 of the catheter is at the attachment site 63. In this embodiment, the lumen of the shorter tube 12 needs to be large enough so than the knots 72 and 67 can be pulled through the tube. The catheter is secured and removed as described previously.

In another embodiment of the attachable catheter 10 as shown in FIG. 4, the distal end of the attachment means 64 already contains a needle 61 at its distal end. The needle 61 and filament 64 of the attachment means are used instead of suture. In FIG. 7 the needle 61 is placed through tissue at a desired attachment site 63 inside the rectum and brought outside the anal opening. The distal end of the filament 64 containing the needle 61 can be placed through and tied to the optional hole 53 in the catheter 65 or tied to the filament at a location along its exposed length, for example at location 73. The needle 61 is cut from the attachment means and discarded. The proximal end of the attachment means 66 is held and the catheter 65 is slid over the attachment means 64 until the distal end 68 of the catheter is at the attachment site 63. The catheter is secured and removed as described previously.

In still another embodiment of the present invention, the distal loop of the attachment means can be fixed directly to the attachment site using resorbable suture or a resorbable clamp. In this embodiment, the catheter is slid up the filament attachment means so that the distal end of the catheter is at the attachment site. The proximal end of the filament attachment means is tied off around the catheter to secure the catheter in place. To remove, the proximal end of the filament attachment means is cut and the catheter is pulled off the filament attachment means. One end of the filament attachment means is then pulled which removes the filament from the suture or clamp attachment at the attachment site. This leaves the resorbable suture or clamp at the attachment site where it will eventually be reabsorbed.

The proximal end of the longer tube of the catheter may be attached to an infusion means to deliver gases, fluids, or medication to the body at the attachment site. Alternatively, the proximal end of the catheter may be attached to a suction means to withdraw gases or fluids from the body at the attachment site. Still further, a fluid delivery tube and fluid withdrawal tube along with the attachment placement tube may be used. In addition, the attachment delivery tube may also be used to feed or withdraw fluids, thus requiring placement of only a signal tube. The proximal end of the catheter may also be left free or placed in a collection bag so that the catheter acts as a drain of body fluids from the attachment site. Still further, while a shorter tube is shown for placement of the attachment means, there is no reason why the tubes can not be of the same length such as in a multilumen catheter.

While attachment to rectal tissue for use following a hemorrhoid procedure was described for illustration purposes, one skilled in the art will recognize that the described device can be used for numerous applications following various medical or surgical procedures. For example, the device has application in ob/gyn procedures, ENT procedures, various abdominal procedures and numerous endoscopic and less invasive procedures where it is desirable to deliver small amounts of topical anesthetic to relieve post surgical pain or discomfort or antibiotics or steroids, to prevent infection or inflammation at the surgical site.

Although this invention has been described in terms of certain preferred embodiments, other embodiments that are apparent to those of ordinary skill in the art are also within the scope of this invention. Accordingly, the scope of the invention is intended to be defined only by reference to the appended claims.

What is claimed is:

1. A multiple tube or multiple lumen catheter for administration or withdrawal of a substance from a human body comprising:

a first lumen or hollow tube for administering or withdrawing a substance, and a second lumen or hollow tube for placement of an attachment means to an attachment site within the body to retain the catheter in the body adjacent the attachment site, said attachment means consisting of a length of filament extending through and beyond proximal and distal ends of the second tube or lumen, said first and second tube being joined together along at least a portion of their length.

2. The catheter of claim 1 wherein the first and second tubes are at least partially enclosed in a third outer joining tube.

3. The catheter of claim 1 wherein the proximal end of one lumen of the catheter is attached to an infusion means for administering a substance into the body at the attachment site of the catheter.

4. The catheter of claim 1 wherein one lumen of the proximal end of the catheter is attached to a suction means for withdrawing a substance from the body at the attachment site of the catheter.

5. The catheter of claim 1 wherein the filament has a loop formed therein, said loop extending from the distal end of the catheter, the filament being tied together at its proximal end and extending from proximal at end of the catheter.

6. A catheter for administering or withdrawing fluid from a body organ comprising:

a tube of a defined length with at least a first and second lumen therethrough, a filament extending along the length of the first lumen and beyond both of distal and proximal ends of the first lumen in the tube, the distal end of the filament having means thereon for attachment to a tissue site within the body organ and the proximal end of the filament having means thereon for securing the filament to the tube when the distal end of the tube is placed adjacent to the tissue site.

7. The catheter of claim 6 having a filament enclosing lumen and a fluid withdrawal lumen.

8. The catheter of claim 6 wherein the means for attachment comprises a loop for receiving and attaching a suture placed through tissue at the tissue site.

9. The catheter of claim 6 wherein the means for attachment comprises a surgical needle attached to the filament.

* * * * *